(12) United States Patent
Ohashi et al.

(10) Patent No.: US 8,106,228 B2
(45) Date of Patent: Jan. 31, 2012

(54) MICROPROTEIN-INACTIVATING ULTRAFINE METAL PARTICLES

(75) Inventors: Kazuaki Ohashi, Yokohama (JP);
Kazuhiro Sato, Yokohama (JP);
Masafumi Toyama, Yokohama (JP);
Munenori Ryo, Osaka (JP); Shigeru Suzuki, Osaka (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 237 days.

(21) Appl. No.: 12/517,914

(22) PCT Filed: Nov. 26, 2007

(86) PCT No.: PCT/JP2007/072736
§ 371 (c)(1),
(2), (4) Date: Jun. 5, 2009

(87) PCT Pub. No.: WO2008/069034
PCT Pub. Date: Jun. 12, 2008

(65) Prior Publication Data
US 2010/0317883 A1    Dec. 16, 2010

(30) Foreign Application Priority Data
Dec. 8, 2006    (JP) .................. 2006-332077

(51) Int. Cl.
*C07F 1/00* (2006.01)
*A61K 9/14* (2006.01)
(52) U.S. Cl. ...................... 556/114; 424/485
(58) Field of Classification Search .................. 556/114; 424/485
See application file for complete search history.

(56) References Cited

U.S. PATENT DOCUMENTS

| 4,289,534 A | 9/1981 | Deffeyes et al. |
| 6,358,611 B1 | 3/2002 | Nagasawa et al. |
| 2005/0112155 A1 | 5/2005 | Giroud et al. |
| 2007/0225409 A1 | 9/2007 | Matsumoto |

FOREIGN PATENT DOCUMENTS

| EP | 0 960 675 A1 | 12/1999 |
| EP | 2 058 066 A1 | 5/2009 |
| JP | 10-183207 A | 7/1998 |
| JP | 2004-210741 A | 7/2004 |
| JP | 2006-241431 A | 9/2006 |
| JP | 2006-291031 A | 10/2006 |
| WO | 03/047636 A2 | 6/2003 |
| WO | 2005/085358 A1 | 9/2005 |

OTHER PUBLICATIONS

Koichi Aoki et al.; "Determination of Structure of Silver Stearate Nanoparticles by Voltammetry," Department of Applied Physics, Fukui University; The Electrochemical Society of Japan Dai 71 Kai Taikai Koen Yoshishu, The Electrochemical Society of Japan; p. 426; Mar. 24, 2004.

Database WPI Week 200574; Thomson Scientific, London, GB AN 2005-725232.

*Primary Examiner* — Porfirio Nazario Gonzalez

(74) *Attorney, Agent, or Firm* — Sughrue Mion, PLLC

(57) ABSTRACT

Microprotein-inactivating ultrafine metal particles comprising ultrafine metal particles having a bond between an organic acid component and a metal, having an infrared absorption peak ascribable to the bond between the organic acid and the metal near 1518 $cm^{-1}$, and capable of efficiently inactivating microproteins without impairing properties of the resin or formability thereof. When used in the form of a resin composition or a coating agent, the microprotein-inactivating ultrafine metal particles are capable of exhibiting an effect for inactivating microproteins.

3 Claims, 4 Drawing Sheets

MICROPROTEIN-INACTIVATING ULTRAFINE METAL PARTICLES

TECHNICAL FIELD

This invention relates to microprotein-inactivating ultrafine metal particles. More specifically, the invention relates to ultrafine metal particles capable of immunologically inactivating microproteins such as allergenic substances, virus and bacteria that are difficult to remove.

BACKGROUND ART

Allergenic substances contained in house dust, usually, comprise plant proteins such as cedar pollens and the like, as well as animal proteins such as mite, its excrements, molds, etc. The allergenic substances are present being adhered to the carpets, curtains, bedclothes, etc. in the houses and offices or being suspended in the air in the rooms.

The allergenic substances are, usually, removed by physical means such as using a vacuum cleaner or an air cleaner. Even with these methods, however, it is difficult to completely remove minute substances.

It can be proposed to use a substance that is capable of immunologically inactivating allergenic substances. For example, there have been proposed an allergen-neutralizing composition containing an effective amount of a substance capable of reducing or cleaving disulfide bond of allergenic proteins, such as thioglycolic acid, 2-mercaptoethanol or polyphenol compound, and a solvent (patent document 1), and an allergen-inactivating agent containing a highly allergenic metal component comprising silver and/or zinc (patent document 2). There has, further, been proposed a microprotein-inactivating material comprising an inorganic porous crystal/hydrophilic high molecular composite material containing, in the hydrophilic high molecules, inorganic porous crystals carrying antibacterial metal ions (patent document 3).

Patent document 1: JP-A-2004-210741
Patent document 2: JP-A-2006-241431
Patent document 3: JP-A-2006-291031

DISCLOSURE OF THE INVENTION

Problems that the Invention is to Solve

According to the above patent documents, the substances for inactivating the allergenic substances are obtained in the form of a solution or a dispersion, which is then sprayed, applied or infiltrated into the carpets, curtains or clothes. Therefore, these substances are not sufficiently fixed to the base materials, and their effect cannot be still sustained to a satisfactory degree.

If the same effect can be obtained by blending a resin forming the articles with the above substances instead of applying the above substances onto the formed articles, then a greater advantage can be obtained in productivity and in sustaining the effect.

It is therefore an object of the present invention to provide microprotein-inactivating ultrafine metal particles that are capable of more efficiently inactivating microproteins and are capable of exhibiting excellent microprotein-inactivating effect in the form of a resin composition or a coating agent.

Means for Solving the Problems

According to the present invention, there are provided microprotein-inactivating ultrafine metal particles comprising ultrafine metal particles having a bond between an organic acid component and a metal.

In the microprotein-inactivating ultrafine metal particles of the present invention, it is desired that:

1. An infrared absorption peak ascribable to a bond between the organic acid and the metal is exhibited near 1518 $cm^{-1}$;
2. The organic acid is a fatty acid; and
3. The metal is at least one of gold, silver or copper.

According to the present invention, there is, further, provided a resin composition containing the microprotein-inactivating ultrafine metal particles.

According to the present invention, further, there is provided a coating agent containing the microprotein-inactivating ultrafine metal particles.

According to the present invention, further, there is provided a solution in which the microprotein-inactivating ultrafine metal particles are dispersed.

Effects of the Invention

Owing to being formed as nano-particulate/nano-dispersed ultrafine metal particles and being bonded to an organic acid, the microprotein-inactivating ultrafine metal particles of the invention are capable of more effectively inactivating the microproteins.

Further, the microprotein-inactivating ultrafine metal particles of the present invention can be prepared in the form of a resin composition or a coating agent that is obtained by nano-dispersing the ultrafine metal particles in a resin or a coating solution so that the ultrafine metal particles can be contained in the formed resin articles or in the films in addition to being prepared as a solution containing the microprotein-inactivating ultrafine metal particles that can be sprayed or applied onto the formed articles.

The resin composition and the coating agent of the invention make it possible to directly obtain formed articles or coatings having the microprotein-inactivating effect. Therefore, the thus formed articles and the coatings excellently sustain the effect since they are free from a problem in regard to fixing a substance (ultrafine metal particles) having antibacterial effect or allergenic substance-inactivating effect like the formed articles onto which a substance having antibacterial effect or allergenic substance-inactivating effect is sprayed, applied or infiltrated.

The microprotein-inactivating ultrafine metal particles of the invention are capable of effectively inactivating the above-mentioned bacteria and allergenic substances, as well as other bacteria, true fungi, and microproteins such as enzymes having a particular steric structure due to the amino acid arrangement, and virus which are particulate substances comprising DNA or RNA (nucleic acid) and a small number of protein molecules.

BEST MODE FOR CARRYING OUT THE INVENTION

According to the invention, an important feature resides in that the microprotein-inactivating ultrafine metal particles comprise ultrafine metal particles having a bond between an organic acid component and a metal.

So far, it has been proposed to use metal ions such as of silver for suppressing the propagation of bacteria and for inactivating allergenic substances such as cedar pollens as well as allergenic substances which are microproteins stemming from the excrements and dead bodies of mite and cockroach. In the present invention, it was found that microproteins can be further effectively inactivated by using ultrafine metal particles having particle sizes of not larger than 1000 nm.

That is, the ultrafine metal particles having particle sizes of not larger than 1000 nm have properties greatly different from those of the ordinary metal particles and, particularly, have high surface activities and large surface areas exhibiting excellent reactivity with the microproteins, making it possible to more effectively decompose the microproteins than when ordinary metal particles are used and exhibiting excellent effect for inactivating the microproteins.

On the other hand, the ultrafine metal particles used in the invention have very high surface activities and, if contained in a resin, accelerate the decomposition of the resin to seriously impair the formability of the resin, which is a disadvantage. According to the present invention, however, an organic acid component is made present on the surfaces of the ultrafine metal particles making it possible to lower the direct contact between the metal surfaces and the resin, to effectively suppress the decomposition of the resin and to suppress a decrease in the molecular weight of the resin so will not to impair the formability. Besides, upon making present the organic acid component on the surfaces of the ultrafine metal particles, more excellent effect for inactivating the microproteins can be exhibited than when a simple metal is used, offering an unexpected effect.

Here, if the ultrafine metal particles have a bond between the organic acid component and the metal can be learned by examining an infrared absorption peak. In the present invention, the infrared absorption peak ascribable to the bond (COO-M) between the organic acid and the metal near 1518 cm$^{-1}$ makes it clear that the ultrafine metal particles have a bond between the organic acid component and the metal.

The above excellent effects of the microprotein-inactivating ultrafine metal particles of the invention will also become obvious from Examples described later.

That is, none of mite allergen-inactivating effect, enzyme-inactivating ratio or antibacterial effect is obtained to a satisfactory degree by the films comprising a resin blended with particles of single silver of an average particle size of 4.5 μm (Comparative Examples 2 and 5). Further, the films of a resin blended with ultrafine silver particles having an average particle size of 100 nm which is in the same range as the ultrafine metal particles of the invention, exhibit improved enzyme-inactivating ratio as compared to those having an average particle size of 4.5 μm but still exhibit the same results as the film containing particles of single silver having a large average particle size with respect to the mite allergen-inactivating effect and antibacterial effect (Comparative Examples 3 and 6). On the other hand, microprotein-inactivating ultrafine metal particles of the invention having an organic acid component on the surfaces of the ultrafine metal particles exhibit very excellent results concerning all of mite allergen-inactivating effect, enzyme-inactivating ratio and antibacterial effect (Examples 1 to 20).

Further, the microprotein-inactivating ultrafine metal particles of the invention can be directly formed as nano-particles and nano-dispersed in the resin. That is, according to the present invention, it was discovered that an organometal salt turns into ultrafine metal particles upon undergoing self-reduction or thermal decomposition through a step of heat-forming a resin or a step of forming a coating, and it was attempted to blend a resin with the organometal salt, turn the organometal salt into nano-particles through the thermal decomposition by conducting the kneading by using an extruder or by firing the coating agent, and nano-disperse the nano-particles without permitting them to be aggregated again, making it possible to efficiently form nano-particulate/nano-dispersed ultrafine metal particles simultaneously with the forming.

Figure 2:
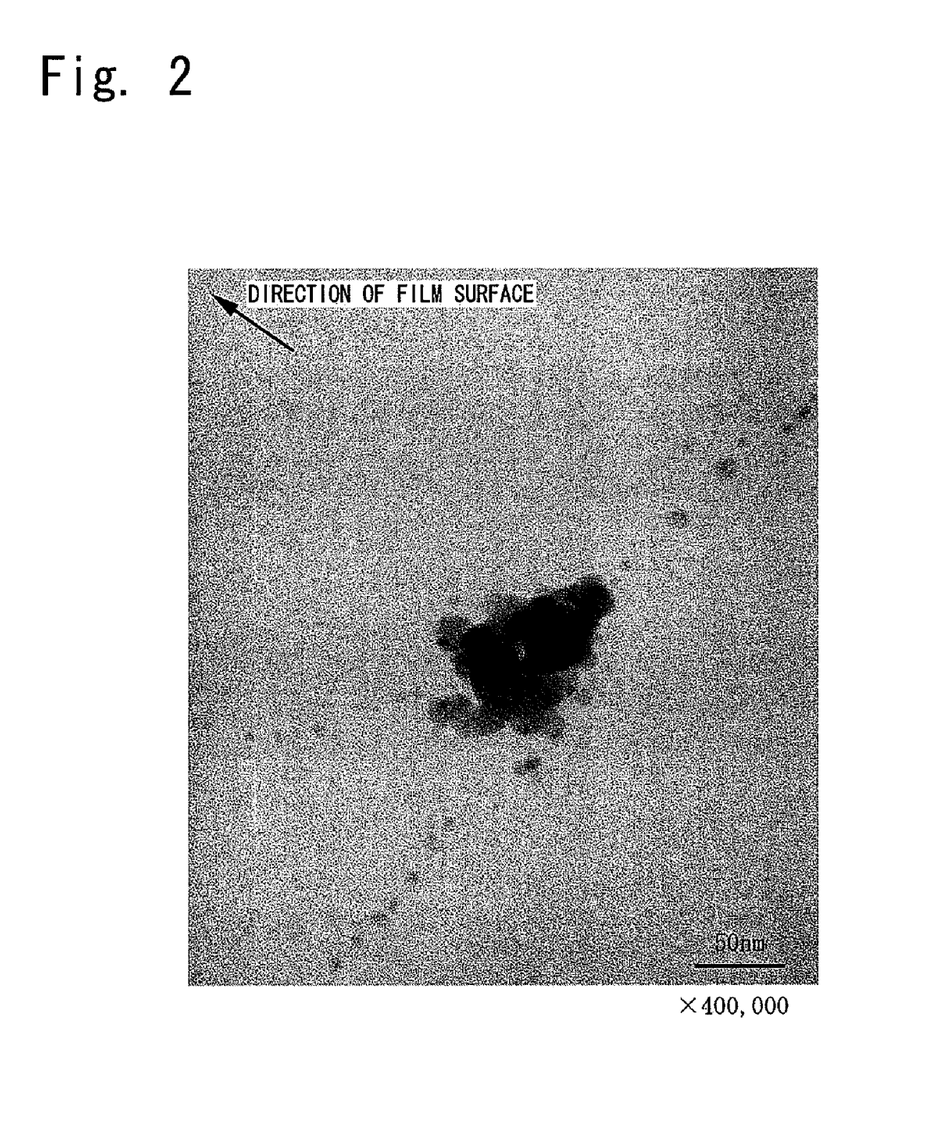
[FIG. 2] is a transmission type electron microphotograph of a cross section of a film obtained in Example 7.
Figure 3:
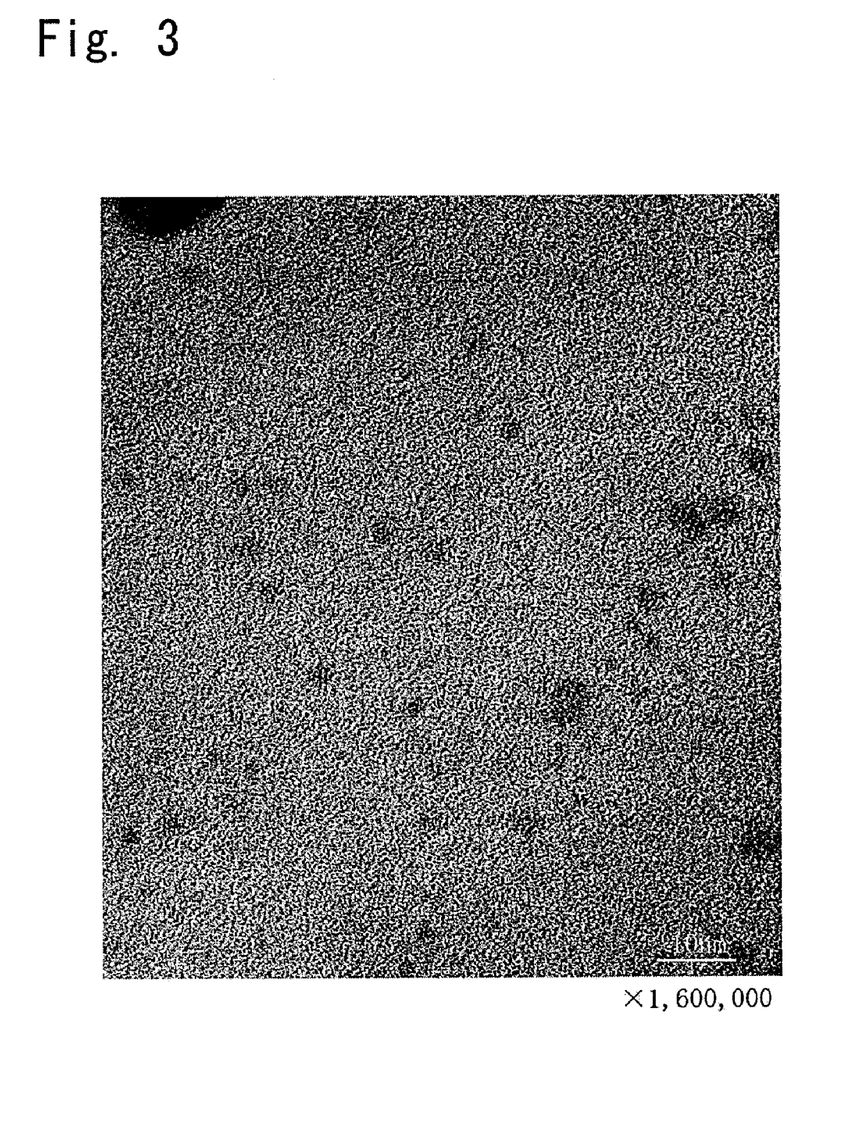
[FIG. 3] is a transmission type electron microphotograph of a cross section of a film obtained in Example 19.
Figure 4:
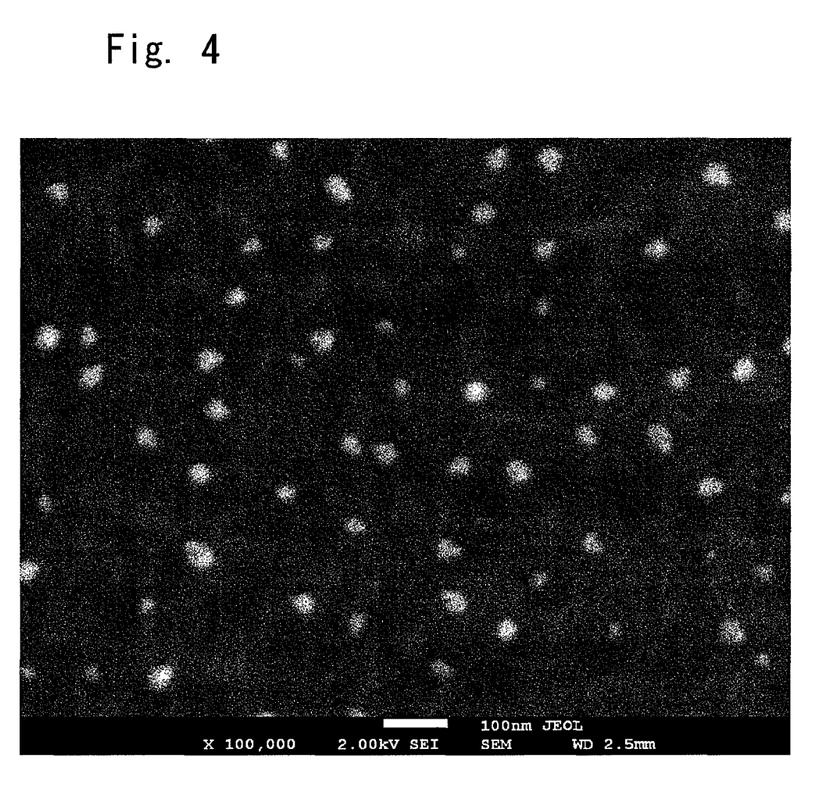
[FIG. 4] is a scanning type electron microphotograph of a surface of a film obtained in Example 13.

This will become obvious from the results of Examples described later. From FIGS. 2 and 3 which are transmission type electron microphotographs of sections of films obtained in Examples 7 and 19, for instance, it is obvious that ultrafine metal particles (dark portions) have been formed (in nano-particulate form) in the film. From FIG. 4 which is a scanning type electron microphotograph of the surface of a film obtained in Example 13, further, it is obvious that ultrafine metal particles (white portions) have been homogeneously and finely dispersed (nano-dispersion).

Figure 1:
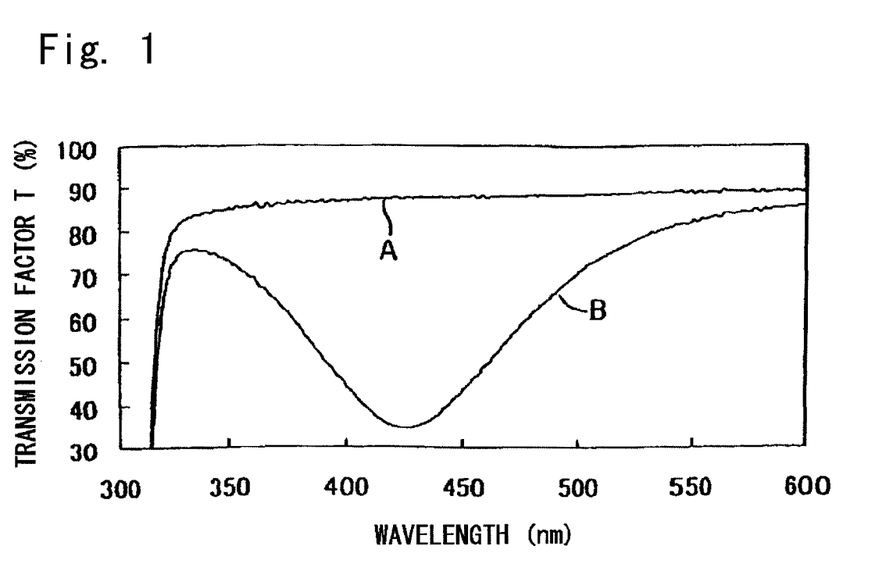
[FIG. 1] is a diagram of spectral transmission factor curves for confirming nano-dispersion.

The ultrafine metal particles that are nano-dispersed in the resin can be confirmed by the presence of plasmon absorption of nano-particles. FIG. 1 shows spectral transmission factor curves of a film comprising a polyethylene terephthalate only and a film obtained by biaxially extruding a polyethylene terephthalate which contains 0.5% by weight of a silver myristate having an average particle size of 100 μm at 270° C. so as to disperse an average particle size of 30 nm. It will be obvious from FIG. 1 that the single polyethylene terephthalate A forms no peak whereas the polyethylene terephthalate B containing the silver myristate exhibits a peak near 400 to 450 nm from which it can be confirmed that the silver particles have been nano-dispersed in the polyethylene terephthalate.

The average particle size referred to in this specification stands for an average of the particles each of which having no gap between the metal and the metal.

(Ultrafine Metal Particles)

In the microprotein-inactivating ultrafine metal particles of the invention, examples of the metal component of ultrafine metal particles include Cu, Ag, Au, In, Pd, Pt, Fe, Ni, Co, Nb, Ru, Rh and Sn. Among them, Au, Ag and Cu are preferred. These metal components may be in a simple form, a mixture or an alloy.

In the present invention as described above, an important feature resides in that the metal has a bond to an organic acid, and exhibits an infrared absorption peak ascribable to the bond between the organic acid and the metal near 1518 cm$^{-1}$.

As the organic acid, there can be exemplified aliphatic carboxylic acids such as myristic acid, stearic acid, oleic acid, palmitic acid, n-decanoic acid, paratoluic acid, succinic acid, malonic acid, tartaric acid, malic acid, glutaric acid, adipic acid and acetic acid; aromatic carboxylic acids such as phthalic acid, maleic acid, isophthalic acid, terephthalic acid, benzoic acid and naphthenic acid; and alicyclic carboxylic acids such as cyclohexanedicarboxylic acid.

In the present invention, it is particularly desired that the organic acid that is used is a higher fatty acid such as myristic acid, stearic acid or palmitic acid and, more particularly desirably, the one having a branch and an increased number of carbon atoms.

As the organometal salt which is a preferred starting substance of the ultrafine metal particles, there can be exemplified, particularly, a silver myristate and a silver stearate. It is, further, desired that their average particle size is in a range of 1 to 500 μm and, particularly, 10 to 200 μm.

The microprotein-inactivating ultrafine metal particles of the present invention are capable of forming ultrafine particles of a single metal by heat-treating an organometal salt which is a starting material of ultrafine metal particles in an inert gas atmosphere. Desirably, however, the organometal salt is mixed with a thermoplastic resin, and is treated with heat to form nano-particulate/nano-dispersed ultrafine metal particles in the resin.

The heating condition required for obtaining ultrafine metal particles used in the invention may differ depending upon the organometal salt that is used, and cannot be exclusively defined but, generally, consists of a temperature of 120 to 350° C. and, particularly, 170 to 300° C. and a period of 30 to 1800 seconds and, particularly, 120 to 600 seconds.

It is desired that the ultrafine metal particles of the invention have a maximum size of less than 1 µm and an average particle size of, particularly, in a range of 1 to 100 nm.

(Resin Compositions)

The resin composition containing the microprotein-inactivating ultrafine metal particles of the invention is a resin composition that is capable of forming a resin article containing ultrafine metal particles, and can be obtained by blending a resin with the ultrafine metal particles that are obtained by heat-treating an organometal salt in an inert atmosphere as described above but is, particularly desirably, a resin composition containing the organometal salt which is a starting substance of the ultrafine metal particles.

That is, as described above, upon the heat treatment at the time of forming the resin composition, the organometal salt which is the starting substance of the microprotein ultrafine metal particles of the invention turns into nano-particulate/nano-dispersed ultrafine metal particles in the formed resin article accounting for the presence of microprotein-inactivating ultrafine metal particles of the invention in the formed resin article.

As the resin for containing microprotein-inactivating ultrafine metal particles of the invention, there can be used any known resin provided it is a thermoplastic resin that can be melt-formed. For example, there can be used olefin resins such as low-, intermediate- or high-density polyethylene, linear low-density polyethylene, linear ultralow-density polyethylene, isotactic polypropylene, syndiotactic polypropylene, propylene/ethylene copolymer, polybutene-1, ethylene/butene-1 copolymer, propylene/butene-1 copolymer and ethylene/propylene/butene-1 copolymer; polyester resins such as polyethylene terephthalate, polybutylene terephthalate and polyethylene naphthalate; polyamide resins such as nylon 6, nylon 6,6, and nylon 6,10; and polycarbonate resins.

It is particularly desired to use the polyethylene, polypropylene or polyester for the resin composition containing the microprotein-inactivating ultrafine particles of the invention.

Depending upon the use, further, the resin composition containing the microprotein-inactivating ultrafine metal particles of the invention may be blended with known blending agents, such as filler, plasticizer, leveling agent, viscosity-imparting agent, viscosity-decreasing agent, stabilizer, antioxidant and ultraviolet ray absorber according to a known recipe.

It is desired that the resin composition containing the microprotein-inactivating ultrafine metal particles of the invention is blended with the organometal salt in an amount of 0.001 to 5 parts by weight per 100 parts by weight of the resin. If the amount thereof is smaller than the above range, the inactivating effect is not obtained to a sufficient degree. If the amount thereof is larger than the above range, on the other hand, the metal particles may aggregate and cannot be nano-dispersed, which is not desirable.

The resin composition containing the microprotein-inactivating ultrafine metal particles of the invention can be obtained in a form that meets the use of the finally formed article, i.e., a formed resin article such as granules, pellets, fiber, film, sheet or container upon being subjected to a known melt-forming, such as two-roll method, injection forming, extrusion forming or compression forming.

The temperature for forming the resin article may vary depending upon the forming method and the kinds of the resin and the organometal salt that are used, and cannot be exclusively specified but must be such a temperature that does not thermally deteriorate the resin that is used and must lie in the above-mentioned range in which the organometal salt can be formed into nano-particulate/nano-dispersed ultrafine metal particles.

The resin composition containing the microprotein-inactivating ultrafine metal particles of the invention may by itself constitute a formed resin article but may, further, constitute a multi-layer structure in combination with other resin.

The formed resin article obtained from the resin composition containing the microprotein-inactivating ultrafine metal particles of the invention, is capable of effectively inactivating plant protein allergenic substances such as cedar pollen and enzymes or viruses, can be formed into nano-particulate/nano-dispersed ultrafine metal particles simultaneously with the forming, and can be excellently produced.

(Coating Agents)

The coating agent containing the microprotein-inactivating ultrafine metal particles of the invention is a coating agent capable of forming a coating containing the microprotein-inactivating ultrafine metal particles of the invention, and may be the one obtained by blending a coating component with the ultrafine metal particles obtained by heat-treating the organometal salt in an inert atmosphere as described above but is, particularly preferably, a coating agent containing the organometal salt which is a starting substance of the above-mentioned ultrafine metal particles.

That is, as described above, the organometal salt which is the starting substance of the microprotein-inactivating ultrafine metal particles of the invention, turns into nano-particles and is nano-dispersed in the coating component through the heat treatment at the time of firing the coating accounting for the presence of the microprotein-inactivating ultrafine metal particles of the invention in the coating.

It is desired that the organometal compound such as the organometal salt is blended in an amount of 0.001 to 5 arts by weight per 100 parts by weight of the coating component. If the amount thereof is smaller than the above range, the microproteins cannot be inactivated to a sufficient degree. If the amount thereof is larger than the above range, on the other hand, the ultrafine metal particles may aggregate, which is not desirable.

There can be used various coating components for containing the microprotein-inactivating ultrafine metal particles of the invention provided they are capable of forming a coating upon heating. For example, though not limited thereto only, there can be used known coating compositions such as acrylic coating material, epoxy coating material, phenol coating material, urethane coating material, polyester coating material and alkyd resin coating material.

Like the resin composition, further, the coating agent can be blended with known blending agents depending upon the use, such as leveling agent, viscosity-imparting agent, viscosity-decreasing agent, stabilizer, antioxidant, ultraviolet ray absorber and colorant according to a known recipe.

The condition for heat-treating the coating agent may vary depending upon the kinds of the coating component and the organometal salt that are used, and cannot be exclusively specified. It is, however, necessary to conduct the heat treatment at a temperature that does not thermally deteriorate the coating composition that is used and in the above-mentioned temperature range in which the organometal salt can be turned into nano-particles and is nano-dispersed for 60 to 600 seconds.

The coating obtained from the coating agent of the invention has an excellent effect for inactivating the microproteins, forming nano-particles which are nano-dispersed simultaneously with the formation of the coating, and can be excellently produced.

(Solutions)

The solution containing the microprotein-inactivating ultrafine metal particles of the invention is a solution that contains the above-mentioned microprotein-inactivating ultrafine metal particles of the invention, and can be used for the members related to dwellings, such as floors, walls, curtains, carpets and the like, for the fiber products used for air conditions as well as woven fabrics, nonwoven fabrics and the like, and for filtering members such as masks, filters and the like in a manner of being sprayed, applied or infiltrated.

The solution containing the microprotein-inactivating ultrafine metal particles of the invention can be prepared by heat-treating the organometal salt in an inert gas atmosphere to form ultrafine metal particles in advance as described above, and dispersing the particles in the solution. It is desired that the ultrafine metal particles are contained in the solution in an amount of 0.001 to 20% by weight and, particularly, 0.01 to 10% by weight from the standpoint of inactivating the microproteins.

As the solution for containing the microprotein-inactivating ultrafine metal particles, a known solvent can be used that has heretofore been used as the solution of this kind. Though not limited thereto only, the solvents that can be used are water such as refined water and ion-exchanged water; lower alcohols such as methanol, ethanol, propanol, isopropanol and butanol; general modified alcohols such as methanol-modified, benzole-modified, triol-modified, methyl ethyl ketone-modified, denatonium benzoate-modified and perfume-modified alcohols; glycol monoethyl ether, chloroform, diethyl carbonate, ethyl acetate, ethyl propionate, ethyl butyrate, hexane and modified alcohols such as ethylene industrial ethyl ether; and glycol type solvents such as ethylene glycol monobutyl ether, diethylene glycol monobutyl ether, propylene glycol monomethyl ether, propylene glycol monopropyl ether, propylene glycol monobutyl ether, propylene glycol diethylene glycol monobutyl ether, dipropylene glycol ethylene glycol monobutyl ether, ethylene glycol monophenyl ether, and triethylene glycol monophenyl ether. These solvents can be used alone or in two or more kinds in combination. In the present invention, ethanol can be preferably used and, particularly preferably, an aqueous solution containing ethanol at a concentration of 1 to 30% can be used.

EXAMPLES

I. Measurement of Particle Size.

Films obtained in Examples 1 to 9, 11 to 19 and in Comparative Examples 1 to 7, as well as primer coatings of primer-coated films obtained in Examples 10 and 20, were sectionally sliced, and were observed by using a transmission type electron microscope (TEM) to take TEM photographs of the ultrafine metal particles therein (as representative examples, FIGS. 2 and 3 show the TEM photographs of Examples 7 and 19). The ultrafine metal particles shown in the photographs were measured for their average particle size by using an image-analyzing software for measuring particle profile: mac-view.

(Method of Evaluation)

II. Confirming the Effect for Inactivating Mite Allergen (Mite Scan).

By using a Mite Scan (manufactured by Asahi Food and Healthcare Co.), it was attempted to confirm the effect for inactivating the Der f I (manufactured by Asahi Food and Healthcare Co.) (allergen contained in the mite body). To confirm the inactivating effect, the presence of mite antigen was confirmed, the films of a resin containing the ultrafine metal particles and the primer-coated films were contacted to and immersed in the antigen, and the effect for inactivating the mite allergen was confirmed based on the following mite scan criteria.

1. Confirming the Presence of Mite Allergen.

(1) Mite antigen solution: A Der f I solution was added in an amount of 20 μL (amount of mite antigen of 2 μg) to a PP Tube (manufactured by BIO-BIK Co.) and was incubated at 37° C. for 2 hours.

(2) Confirming the presence of mite antigen: After incubated, the solution was dropped onto the mite scan measuring portion, and the presence of the mite antigen was confirmed relying upon the coloring amounts of a C-line and a T-line described below.

2. Confirming the Effect for Inactivating the Mite Allergen.

(1) Film samples: The films obtained in Examples 1 to 9, 11 to 19 and Comparative Examples 1 to 7, and the primer-coated films obtained in Examples 10 and 20 were cut into short strips 5 mm wide and 100 mm long, and were used as film samples.

(2) Contact/immersion: The Der f I solution was added in an amount of 20 μL (amount of mite antigen of 2 μg) to the PP Tube (manufactured by BIO-BIK Co.), and the film samples were inserted so as to be contacted and immersed, and were incubated at 37° C. for 2 hours.

(3) Determination: After incubated, the film samples were removed, the solutions were dropped onto the mite scan measuring portion, and the effect of inactivation was confirmed relying upon the coloring amounts of the C-line and the T-line described below.

3. Mite Scan Criteria.

1. There is no mite allergen contamination (quite no C-line coloring or T-line coloring).
2. Slightly contaminated with mite allergen (C-line coloring>T-line coloring).
3. Contaminated with mite allergen (C-line coloring=T-line coloring).
4. Very contaminated with mite allergen (C-line coloring<T-line coloring).

III. Confirming the Effect for Inactivating Enzymes.

The effect for inactivating the enzymes was confirmed by using a β-galactosidase. To confirm the inactivating effect described above, an initial value was plotted when the presence of an enzyme was confirmed, a sample value was plotted by contacting and immersing the film of a resin containing the ultrafine metal particles, and the effect was confirmed by calculating the ratio of inactivating the enzymes described below. The activity of the enzymes was measured by using the β-Galactosidase Enzyme Assay System with Reporter Lysis Buffer (manufactured by Promega Co.) which was an attached sample.

1. Confirming the Presence of an Initial Enzyme.

(1) Preparation of an enzyme solution: Diluted with a 1× Reporter Lysis Buffer so that the concentration of β-galactosidase was 0.1 μL/1 mL.

(2) Pretreatment: 50 μL of the β-galactosidase solution (0.1 μL/1 mL) was added to the PP Tube (manufactured by BIO-BIK Co.) and was incubated at 37° C. for 2 hours. Thereafter, the 1× Reporter Lysis Buffer was mixed in an amount of 100 μL thereto.
(3) Color-developing reaction: The Assay Buffer was dropped in an amount of 150 μL, mixed and was, thereafter, reacted in a hot bath at 37° C. for 30 minutes.
(4) Terminating the reaction: 500 μL of 1M sodium carbonate was mixed to terminate the reaction.
(5) Measuring the absorbance: The absorbance at 420 nm of the solution was measured and was regarded to be an initial value.

2. Confirming the Effect of the Samples for Inactivating Enzymes.
(1) Adjusting the enzyme solution: Diluted with the 1× Reporter Lysis Buffer so that the concentration of the β-galactosidase was 0.1 μL/1 mL.
(2) Contact/immersion: 100 μL of a β-galactosidase solution (0.1 μL/1 mL) was added to the PP Tube, and the sample film (3 mm wide, 20 mm long) was inserted in the PP Tube so as to be contacted and immersed in the solution and was incubated at 37° C. for 2 hours. After the film has been removed, 50 μL of the solution was picked up and was mixed into 100 μL of the 1× Reporter Lysis Buffer.
(3) Color-developing reaction: The Assay Buffer was dropped in an amount of 150 μL, mixed and was, thereafter, reacted in a hot bath at 37° C. for 30 minutes.
(4) Terminating the reaction: After 30 minutes have passed, 500 μL of 1M sodium carbonate was mixed to terminate the reaction.
(5) Measuring the absorbance: The absorbance at 420 nm of the solution was measured and was regarded to be a sample value.

3. Calculating the Ratio of Inactivating Enzymes.
By using the measured initial values and sample values, the ratios of inactivating the enzymes of the samples were found in compliance with the following formula.

(Enzyme-inactivating ratio)=(1−sample value/initial value)×100(%)

IV. Confirming the Antibacterial Effect.
By using the films obtained in Examples 1 to 9, 11 to 19 and Comparative Examples 1 to 7, as well as the primer-coated films obtained in Examples 10 an 20, the antibacterial effects were confirmed in compliance with the JIS Z 2801. The species was the *Escherichia coli*. A logarithmic value of a number obtained by dividing the number of bacteria after the untreated film was cultured by the number of bacteria after the antibacterial film was cultured, was regarded to be an antibacterially active value. The antibacterial effect was regarded to be ○ when the antibacterially active value was not smaller than 2.0 and was regarded to be X when it was smaller than 2.0. Though the antibacterial effect was not confirmed for the *S. aureus*, it is estimated that the antibacterial effect is the same as for the *Escherichia coli*.

V. Confirming the Infrared Ray Absorption Peak Near 1518 $cm^{-1}$.
Relying upon a total reflection measuring method which is a customary method by using a Fourier transform type infrared spectrophotometer (manufactured by Digi-Labo Japan Co.), the films obtained in Examples 1 to 9, 11 to 19 and Comparative Examples 1 to 7 as well as the primer coatings of the primer-coated films obtained in Examples 10 and 20 were confirmed for their infrared absorption peaks near 1518 $cm^{-1}$ ascribable to a bond between the organic acid component and the metal.

VI. Evaluating the Appearance.
The films obtained in Examples 1 to 9, 11 to 19 and Comparative Examples 1 to 7, as well as the primer-coated films obtained in Examples 10 and 20 were confirmed for the presence of aggregates of particles by naked eyes. Those without aggregation and having excellent appearance were regarded to be ○ and those having aggregations and poor appearance were regarded to be X.

Example 1

5 Kilograms of a low-density polyethylene resin was blended with a silver stearate of an average particle size of 100 μm in such an amount that the content thereof was 1.5 wt %, and was extruded by using a biaxial extruder (manufactured by Toyo Seiki Seisakusho, LTD.) at an extrusion-forming temperature of 220° C. to prepare a film of a thickness of 50 μm.
The film was confirmed for its effect for inactivating mite allergen, effect for inactivating enzymes and infrared ray absorption peak near 1518 $cm^{-1}$, and was evaluated.

Example 2

A film was prepared in the same manner as in Example 1 but changing the content of the silver stearate to be 1.0 wt %, and was confirmed and evaluated.

Example 3

A film was prepared in the same manner as in Example 1 but changing the content of the silver stearate to be 0.5 wt %, and was confirmed and evaluated.

Example 4

A film was prepared in the same manner as in Example 1 but setting the extrusion-forming temperature at 250° C., and was confirmed and evaluated.

Example 5

A film was prepared in the same manner as in Example 1 but setting the extrusion-forming temperature at 270° C., and was confirmed and evaluated.

Example 6

A film was prepared in the same manner as in Example 1 but using a silver myristate of an average particle size of 100 μm, and was confirmed and evaluated.

Example 7

A film was prepared in the same manner as in Example 6 but changing the content of the silver myristate to be 0.5 wt %, and was confirmed and evaluated.

Example 8

A film was prepared in the same manner as in Example 6 but setting the extrusion-forming temperature at 250° C., and was confirmed and evaluated.

Example 9

A film was prepared in the same manner as in Example 6 but setting the extrusion-forming temperature at 270° C., and was confirmed and evaluated.

Example 10

A high molecular bisphenol type epoxy resin, a phenol-formaldehyde resin (resol type) solution, a curing catalyst (phosphoric acid) and a silver myristate of an average particle size of 100 μm were stirred and mixed at a resin component ratio of 46:46:3:5, and from which a primer was prepared by using a mixed solvent (cyclohexanone:MIBK:MEK=1:1:1) so that the concentration of the coating resin component was 20%. Onto a biaxially oriented PET/I (terephthalic acid/isophthalic acid=88/12) copolymerized polyester film of a thickness of 50 μm, the primer was applied in a manner that the dry weight thereof was 0.6 g/m$^2$, followed by drying at 180° C. to prepare a primer-coated film which was, then, confirmed and evaluated.

Comparative Example 1

5 Kilograms of a low-density polyethylene resin was extruded by using a biaxial extruder (manufactured by Toyo Seiki Seisakusho, LTD.) at an extrusion-forming temperature of 220° C. to prepare a film of a thickness of 50 μm. The film was confirmed for its effect for inactivating mite allergen, effect for inactivating enzymes and infrared ray absorption peak near 1518 cm$^{-1}$, and was evaluated.

Comparative Example 2

A film was prepared in the same manner as in Example 1 but blended with the silver of an average particle size of 4.5 μm in an amount 0.5 wt %, and was confirmed and evaluated.

Comparative Example 3

A film was prepared in the same manner as in Example 1 but blended with the silver of an average particle size of 100 nm in an amount 0.5 wt %, and was confirmed and evaluated.

Comparative Example 4

A film was prepared in the same manner as in Example 1 but blended with the silver stearate of particle sizes of 1 to 100 nm in an amount 0.5 wt %, the silver stearate being the one obtained by heating a conventionally formed silver stearate in an inert gas atmosphere at a temperature of 250 degrees. The film was measured, calculated, confirmed and evaluated.

Table 1 shows the above-mentioned effects for inactivating mite allergen, effects for inactivating enzymes, infrared ray absorption peaks near 1518 cm$^{-1}$ that were confirmed, appearances and evaluated results.

From the above Examples and Table 1, it will be learned that the inactivating ultrafine metal particles of the invention are effective in inactivating microproteins such as allergen, viruses, etc.

TABLE 1

|  | Composition (starting material) | Content of ptcls. (wt %) | Extrusion-forming temp. (° C.) | Ave. ptcl. size after extrusion-formed (nm) | Effect for inactivating mite allergen |
|---|---|---|---|---|---|
| Ex. 1 | silver stearate | 1.5 | 220 | 12 | 1 |
| Ex. 2 | silver stearate | 1.0 | 220 | 15 | 1 |
| Ex. 3 | silver stearate | 0.5 | 220 | 11 | 1 |
| Ex. 4 | silver stearate | 1.5 | 250 | 15 | 1 |
| Ex. 5 | silver stearate | 1.5 | 270 | 20 | 1 |
| Ex. 6 | silver myristate | 1.5 | 220 | 8 | 1 |
| Ex. 7 | silver myristate | 0.5 | 220 | 12 | 1 |
| Ex. 8 | silver myristate | 1.5 | 250 | 15 | 1 |
| Ex. 9 | silver myristate | 1.5 | 270 | 20 | 1 |
| Ex. 10 | silver myristate | 1.0 | 180* | 100 | 1 |
| Comp. Ex. 1 | none | 0 | 220 | — | 3 |
| Comp. Ex. 2 | silver | 0.5 | 220 | 5000 | 3 |
| Comp. Ex. 3 | silver | 0.5 | 220 | 1000 | 3 |
| Comp. Ex. 4 | silver stearate | 0.5 | 220 | 150 | 3 |

|  | Enzyme inactivating ratio (%) | Infrared absorption peak near 1518 cm$^{-1}$ | Appearance |
|---|---|---|---|
| Ex. 1 | 99 | ○ | ○ |
| Ex. 2 | 99 | ○ | ○ |
| Ex. 3 | 99 | ○ | ○ |
| Ex. 4 | 99 | ○ | ○ |
| Ex. 5 | 99 | ○ | ○ |
| Ex. 6 | 99 | ○ | ○ |
| Ex. 7 | 99 | ○ | ○ |
| Ex. 8 | 99 | ○ | ○ |
| Ex. 9 | 99 | ○ | ○ |
| Ex. 10 | 80 | ○ | ○ |
| Comp. Ex. 1 | 0.4 | X | X |
| Comp. Ex. 2 | 1 | X | X |
| Comp. Ex. 3 | 10 | X | X |
| Comp. Ex. 4 | 40 | X | X |

*drying temperature

Example 11

5 Kilograms of a low-density polyethylene resin was blended with a silver stearate of an average particle size of 100 μm in such an amount that the content thereof was 0.1 wt %, and was extruded by using a biaxial extruder (manufactured by Toyo Seiki Seisakusho, LTD.) at an extrusion-forming temperature of 220° C. to prepare a film of a thickness of 50 μm. The film was calculated for its antibacterially active value, confirmed for its antibacterial effect and infrared ray absorption peak near 1518 $cm^{-1}$, and was evaluated.

Example 12

A film was prepared in the same manner as in Example 11 but changing the content of silver stearate to be 0.5 wt %, and was calculated, confirmed and evaluated.

Example 13

A film was prepared in the same manner as in Example 11 but changing the content of silver stearate to be 1.0 wt %, and was calculated, confirmed and evaluated.

Example 14

A film was prepared in the same manner as in Example 11 but changing the content of silver stearate to be 1.5 wt %, and was calculated, confirmed and evaluated.

Example 15

A film was prepared in the same manner as in Example 14 but setting the extrusion-forming temperature at 200° C., and was calculated, confirmed and evaluated.

Example 16

A film was prepared in the same manner as in Example 14 but setting the extrusion-forming temperature at 270° C., and was calculated, confirmed and evaluated.

Example 17

A film was prepared in the same manner as in Example 11 but using a polypropylene resin, and was calculated, confirmed and evaluated.

Example 18

A film was prepared in the same manner as in Example 11 but changing the content of silver myristate of an average particle size of 100 μm to be 0.1 wt %, and was confirmed and evaluated.

Example 19

A film was prepared in the same manner as in Example 11 but changing the content of silver myristate of an average particle size of 100 μm to be 1.5 wt %, and was confirmed and evaluated.

Example 20

A high molecular bisphenol type epoxy resin, a phenol-formaldehyde resin (resol type) solution, a curing catalyst (phosphoric acid) and a silver stearate of an average particle size of 100 μm were stirred and mixed at a resin component ratio of 46:46:3:5, and from which a primer was prepared by using a mixed solvent (cyclohexanone:MIBK:MEK=1:1:1) so that the concentration of the coating resin component was 20%. Onto a biaxially oriented PET/I(terephthalic acid/isophthalic acid=88/12) copolymerized polyester film of a thickness of 50 μm, the primer was applied in a manner that the dry weight thereof was 0.6 $g/m^2$, followed by drying at 180° C. to prepare a primer-coated film which was, then, confirmed and evaluated.

Comparative Example 5

A film was prepared in the same manner as in Example 11 but blended with the silver of an average particle size of 4.5 μm in an amount 1.0 wt %, and was confirmed and evaluated.

Comparative Example 6

A film was prepared in the same manner as in Example 11 but blended with the silver of an average particle size of 100 nm in an amount 1.0 wt %, and was confirmed and evaluated.

Comparative Example 7

A film was prepared in the same manner as in Example 1 but blended with the silver stearate of an average particle size of 100 nm in an amount 0.5 wt %, the silver stearate being the one obtained by heating a conventionally formed silver stearate in an inert gas atmosphere at a temperature of 250° C. The film was measured, calculated, confirmed and evaluated. The results were as shown in Table 2.

Tables 1 and 2 show the above-mentioned antibacterially active values, antibacterial effects and infrared ray absorption peaks near 1518 $cm^{-1}$ that were confirmed, appearances and evaluated results.

TABLE 2

| | Composition (starting material) | Content of ptcls. (wt %) | Extrusion-forming temp. (° C.) | Ave. ptcl. size after extrusion-formed (nm) |
|---|---|---|---|---|
| Ex. 11 | silver stearate | 0.1 | 220 | 8 |
| Ex. 12 | silver stearate | 0.5 | 220 | 11 |
| Ex. 13 | silver stearate | 1.0 | 220 | 15 |
| Ex. 14 | silver stearate | 1.5 | 220 | 8 |
| Ex. 15 | silver stearate | 1.5 | 200 | 10 |
| Ex. 16 | silver stearate | 1.5 | 270 | 20 |
| Ex. 17 | silver stearate | 0.1 | 220 | 10 |
| Ex. 18 | silver myristate | 0.1 | 220 | 10 |
| Ex. 19 | silver myristate | 1.5 | 220 | 9 |
| Ex. 20 | silver stearate | 1.0 | 180* | 100 |
| Comp. Ex. 5 | silver | 1.0 | 220 | 5000 |
| Comp. Ex. 6 | silver | 1.0 | 220 | 1000 |
| Comp. Ex. 7 | silver stearate | 0.5 | 220 | 150 |

| | *Escherichia coli* Antibacterially active value | Infrared absorption peak near 1518 $cm^{-1}$ | Appearance |
|---|---|---|---|
| Ex. 11 | 2.1 | ◯ | ◯ |
| Ex. 12 | 2.5 | ◯ | ◯ |
| Ex. 13 | 4.0 | ◯ | ◯ |
| Ex. 14 | 6.0 or more | ◯ | ◯ |
| Ex. 15 | 6.0 or more | ◯ | ◯ |
| Ex. 16 | 6.0 or more | ◯ | ◯ |
| Ex. 17 | 2.1 | ◯ | ◯ |
| Ex. 18 | 2.1 | ◯ | ◯ |

TABLE 2-continued

| | | | | |
|---|---|---|---|---|
| Ex. 19 | 6.0 or more | ○ | ○ | ○ |
| Ex. 20 | 2.2 | ○ | ○ | ○ |
| Comp. Ex. 5 | 1.0 | X | X | X |
| Comp. Ex. 6 | 1.0 | X | X | X |
| Comp. Ex. 7 | 1.5 | X | X | X |

*drying temperature

The invention claimed is:

1. A microprotein-inactivating resin composition comprising a resin and ultrafine metal particles of an average particle size of 1 to 100 nm having a bond between an organic acid component and a metal, said ultrafine metal particles being formed in the resin by blending the resin with a fatty acid metal salt followed by heating.

2. The microprotein-inactivating resin composition according to claim 1, wherein an infrared absorption peak ascribable to a bond between said organic acid and the metal is exhibited near 1518 $cm^{-1}$.

3. The microprotein-inactivating resin composition according to claim 1, wherein said metal is at least one of gold, silver or copper.

* * * * *